(12) United States Patent
Heinsohn et al.

(10) Patent No.: US 6,167,652 B1
(45) Date of Patent: Jan. 2, 2001

(54) METHOD FOR TREATING COTYLEDONOUS PLANTS

(75) Inventors: George E. Heinsohn, Elkton, MD (US); August S. Bjornson, Wilmington, DE (US)

(73) Assignee: DCV, Inc., Wilmington, DE (US)

( * ) Notice: Under 35 U.S.C. 154(b), the term of this patent shall be extended for 0 days.

(21) Appl. No.: 09/237,065

(22) Filed: Jan. 26, 1999

Related U.S. Application Data

(63) Continuation-in-part of application No. 09/013,945, filed on Jan. 27, 1998, now abandoned, which is a continuation-in-part of application No. 08/787,870, filed on Jan. 23, 1997, now abandoned.

(51) Int. Cl.$^7$ .............................. A01B 79/00; C05F 1/00; C08B 37/00; A01N 43/04

(52) U.S. Cl. ..................... 47/58.1; 504/100; 504/118; 504/140; 504/292; 71/16; 71/27; 536/20; 514/55

(58) Field of Search ............................. 47/58.1; 504/100, 504/118, 140, 292; 71/16, 27; 536/20; 514/55

(56) References Cited

U.S. PATENT DOCUMENTS

| | | | |
|---|---|---|---|
| 4,812,159 | 3/1989 | Freepons | 504/147 |
| 4,886,541 | 12/1989 | Hadwiger | 504/100 |
| 4,964,894 | * 10/1990 | Freepons | 71/88 |
| 4,978,381 | 12/1990 | Hadwiger | 504/292 |
| 5,104,437 | 4/1992 | Hadwiger | 504/292 |
| 5,374,627 | 12/1994 | Ito et al. | 514/55 |
| 5,554,445 | 9/1996 | Struszczuk et al. | 428/403 |

FOREIGN PATENT DOCUMENTS

| | | |
|---|---|---|
| 9 346061 | 7/1995 | (JP) . |
| WO89/07395 | 8/1989 | (WO) . |

* cited by examiner

*Primary Examiner*—Charles L. Patterson, Jr.
*Assistant Examiner*—Tekchand Saidha

(57) ABSTRACT

Application of a water-soluble salt of chitosan to the foliage of growing plants increases the yield of vegetables, tubers, cereal grains, fruits and blossoms. Plants so treated are healthier, sturdier, more resistant to drought and many varieties enjoy an extended period of production. The plants may be effectively and conveniently treated by spraying the foliage with a solution containing 0.01–1.5% wt. chitosan salt using conventional agricultural equipment and techniques.

13 Claims, No Drawings

METHOD FOR TREATING COTYLEDONOUS PLANTS

RELATED APPLICATION

This application is a Continuation-in-Part of U.S. patent application Ser. No. 09/013,945, filed Jan. 27, 1998, now abandoned, which is a Continuation-in-Part of U.S. patent application Ser. No. 08/787,870, filed Jan. 23, 1997, now abandoned.

FIELD OF INVENTION

The Invention is directed to a method for treating cotyledonous plants to improve the yield, health, and vigor of the plant by spraying an aqueous solution of a chitosan salt onto the leaves of the plant.

BACKGROUND OF THE INVENTION

Chitosan is a naturally occurring polymer found in many fungi. It may be broadly described as a copolymer of D-glucosamine and N-acetyl-D-glucosamine in which 65–100% of the monomer units are D-glucosamine. Since it is a member of the chemical class known as amines, which are weakly basic, it readily and reversibly forms salts with acids such as mineral acids and carboxylic acids. Many of these salts are water soluble at acid pH values. In a system in which chitosan and an acid are present, both electrically neutral glucosamine units and units in which the glucosamine unit is protonated and associated with the anion corresponding to the acid will be present in the polymer chain in proportions which are dependent on pH. Such a system is commonly referred to as a chitosan salt without regard to the extent to which the glucosamine units are protonated.

As used herein, the term "chitosan salt" includes not only the chitosan salt, but also any partially unprotonated chitosan which may be present in acidic media.

It has been demonstrated that application of chitosan salt to the seeds of cereal crops results in dramatic changes in the biochemistry of the emergent plant. Included among these changes are an increased production of a class of compounds known as the phytoalexins, which provide protection against localized microbial infection, and increased production of callose and lignin which provide structural strength and a barrier to the spread of infection. These changes occur as a result of activation of the gene encoding the enzyme phenylalanine ammonia lyase, which is involved in the rate determining step of the phenylpropanoid metabolism pathway. The chitosan salt has been shown to induce synthesis of the terpenoid phytoalexins, which are closely involved in the biosynthesis of growth hormones such as gibberelic acid and abscisic acid. Chitosan salt also induces activation of genes which produce chitinase and glucanase enzymes that are known to be both fungal inhibitors and to play a role in pollen development and seed germination. It also induces activation of genes which produce protease inhibitors that help protect the plant from insect attack. These changes result in enhanced root development, reduced lodging (plants falling over before harvest), enhanced yield, and resistance to certain plant diseases.

In U.S. Pat. No. 4,812,159, Freepons discloses, in detail, treatment of soil in the seed planting zone with an aqueous solution of chitosan salt, application of a chitosan salt solution to plant seeds, treatment of soil in the seed planting zone with a mixture of solid chitosan and a solid acid, and treatment of soil in the seed planting zone with a solid chitosan salt. The preferred chitosan salt solution is one that contains more than 1.5 equivalents of glutamic acid per mole of amino function in the chitosan. Application of chitosan salt to the foliage of an emerging plant is mentioned, but there is no disclosure of the methods required to accomplish such treatment, or of the results thereby achieved. For all of these treatments it is stipulated that when an acidic component is used in making the chitosan salt preparation, the acid must be selected from the group of non-phytotoxic acids, which are defined as those acids that will not cause a significant adverse effect on germination of seeds or on development of the seedling, i.e., seed phytotoxicity.

In U.S. Pat. No. 4,964,894, which is a continuation-in-part of U.S. Pat. No. 4,812,159, Freepons notes that glutamic acid, tartaric acid, citric acid, adipic acid, hydrochloric acid, formic acid, and nitric acid meet the criteria of non-phytotoxicity. Acetic acid and butyric acid were found to be phytotoxic and harmful to the development of the plant seedlings. This would make these acids unsuitable for use according to the teachings of Freepons.

According to U.S. Pat. No. 4,812,159, the treatment of seed is accomplished by applying a chitosan preparation to the seed or by immersing the seed in such a preparation, followed by drying. The drying step is necessary to prevent premature germination of the seed in the time interval between the treatment with chitosan and planting. In the absence of a drying step, the patent recommends that planting occur within 60 hours of seed treatment.

While seed treatment is easily accomplished on a small scale using the methods disclosed by Freepons, the treatment protocols are difficult to extend to commercial scale operations without devising specialized equipment or modifying specialized equipment commonly used in the seed coating industry such as grain angering devices like the Gustavson seed coater. This is a serious drawback in commercial operations where the same piece of equipment must also be used to carry out other treatments (e.g., application of fungicides) to seeds and cannot economically be dedicated for use only with chitosan-containing materials. Furthermore, such treatment is limited to a single application of chitosan salt at the very earliest stage of plant growth, which may not be repeated and reinforced at other key stages of plant growth such as seed formation, rapid growth phases, flowering and ripening.

Treatment of soil in the seed planting zone with a chitosan salt preparation requires that the preparation be distributed in a region in close proximity to where the seed will be or has been planted. Specialized equipment is therefore required to limit the treatment to the region where the seed will eventually germinate. While this may be readily accomplished in the case of mechanized seeding, this technique is not compatible with other methods such as aerial seeding or broadcast seeding. In addition, the two techniques utilizing chitosan salt in the form of a solid require that the solid be introduced in the form of very small particles of 0.5–100 micrometers. Therefore, elaborate pre-processing of the chitosan salt is required to put it in a form suitable for application. As with seed treatment, treatment of soil in the region of seed germination is limited to a single treatment at the very earliest stage of plant growth, lest the root system of the plant be disrupted.

While this patent superficially discloses the application of chitosan to the foliage of emerging plants, there are no data to show any beneficial effect. Furthermore, the teaching is limited by implication to the earlier stages of plant growth. Thus, the patent teaches nothing about the treatment of plants having leaves capable of photosynthesis.

In U.S. Pat. No. 4,964,894, Freepons again describes the techniques noted above and then describes an elaborate procedure involving seed germination studies for identifying non-phytotoxic acids. Glutamic acid, tartaric acid, citric acid, adipic acid, hydrochloric acid, formic acid and nitric acid met the criteria for non-phytotoxicity. Acetic acid and butyric acid were found to be phytotoxic and therefore detrimental to development of the seedling. The preferred chitosan salt solution is taught to be one that contains more than 1.5 equivalents of glutamic acid per mole of amino function in the chitosan.

Another seed treating technique is described in U.S. Pat. No. 5,554,445 (Kivekas, Struszczyk), which involves spraying seeds with a liquid dispersion of microcrystalline chitosan, followed by drying to form a film of the chitosan polymer around the seed. In order to form an appropriate film on the seed, the chitosan is specified to have a water retention value of 200–5,000%, hydrogen bonding potential of 10–25 kJ/mol, and particle size of 0.1–100 micrometers. As in the cases noted above, these procedures require specialized equipment, elaborate pre-processing of the chitosan, and are limited to a single treatment at the earliest stage of plant growth.

In U.S. Pat. No. 4,886,541, Hadwiger discloses the application of a chitosan preparation to wheat seed in order to enhance yield, reduce lodging, and enhance root development. Treatment is accomplished by applying an aqueous solution of chitosan acetate to the seed in a manner such that the seed is agitated to distribute the liquid on the seed. Recommended techniques are the use of a grain augering device or cement mixing equipment. As discussed above, application of chitosan to seeds by this method adds complexity and cost to commercial seed coating, and is limited to a single application at the earliest stage of plant growth. In U.S. Pat. Nos. 4,978,381 and 5,104,437 the same techniques for seed treatment are described, which extend the method to other cereal crops such as rice, oats, barley, and rye.

Chitosan has been employed in agriculture for purposes other than its ability to enhance crop yields. It has demonstrated ability as a bactericide against a variety of microorganisms. The use of chitosan to inhibit frost damage is disclosed in JP 99346061 (assigned to Daiichi Seimo KK) wherein spinach leaves inoculated with the ice-nucleating organisms *Pseudomonas syringe* and *Pantoea agglomerants* were treated with chitosan and then exposed to freezing temperature. The treated leaves had significantly less frost damage than the controls. In U.S. Pat. No. 5,374,627, Etsuzo et al disclose the use of a chitosan hydrolysate of molecular weight 10,000–50,000 for protecting plants against a number of plant diseases such as bacterial soft rot (vegetables), spring deadspot (turfgrass), and bacterial grain rot (rice).

SUMMARY OF THE INVENTION

The invention is therefore directed to the application of a chitosan salt to the foliage of growing plants to enhance health, vigor and the yields of vegetables, seeds, fruits, tubers, and blossoms. Plants so treated are healthier, more drought resistant, and many varieties enjoy an extended production period. The treatment may be repeated throughout the growth cycle of the plant, especially during critical stages of plant growth such as flowering, seed formation, and ripening.

More particularly, the invention is directed to a method for improving the yield, health, and vigor of growing cotyledonous plants comprising (1) spraying onto the foliage between appearance of the first true leaves capable of photosynthesis and harvest of the plant or fruit therefrom an aqueous solution containing dissolved therein 0.01–1.5% by weight of a water-soluble salt of chitosan and phytotoxic acid, in which solution the ratio of acid equivalents to amino groups derived from the chitosan is 1.02–1.20, and (2) repeating step (1) at least two times before harvesting the plant or useful portion thereof.

In a still further aspect, the invention is directed to a method for preparing the above-described treating solution comprising (1) forming an aqueous liquid solution having an acidic pH comprising 0.5–6.0 wt. % of a water-soluble salt of chitosan prepared by reaction at an elevated temperature of a water-soluble chitosan, having a molecular weight no higher than about 600,000, with a water-soluble, monobasic organic acid, which may be substituted with other than halogen or amine groups, for a time and at a temperature sufficient to effect substantially complete reaction of the chitosan without degrading the chitosan to an extend that it becomes water-soluble, in which solution the ratio of acid equivalents to amino groups derived from the chitosan is 1.01–1.20; and (2) raising the pH of the chitosan salt solution from step (1) to a level of 4.2–6.2 by diluting the solution with water, having a pH of about 7.

DEFINITION

As used herein, the term "harvest" and various forms thereof refer not only to gathering the useful or edible portion of growing plants, but also to gathering the entire plant. Examples of the former are picking fruit from trees, picking beans from vines, picking ears of corn from the stalks, cutting cabbage and celery, etc. Examples of the latter are the digging of root vegetables such as potatoes, beets, and carrots.

DETAILED DESCRIPTION OF THE INVENTION

A. Composition of Chitosan

Though chitosan is a naturally occurring polymer found in many fungi, it is neither abundant nor readily isolated in high purity from natural sources. As a matter of convenience, chitosan is more readily obtained from chitin which (after cellulose) is the second most abundant natural polymer. Chitin is readily isolated from shellfish or insect exoskeletons, and is also found in mollusks and fungi. It is a water insoluble copolymer of N-acetyl -D- glucosamine and D-glucosamine, but the great preponderance of monomer units consist of N-acetyl-D-glucosamine residues. Chitosan is a copolymer of the same two monomer units, but the preponderance of monomer units are D-glucosamine residues. Since the D-glucosamine residues bear a basic amino function, they readily form salts with acids. Many of these salts are water soluble. Treatment of chitin with concentrated caustic at elevated temperature converts N-acetyl-D-glucosamine residues into D-glucosamine residues and thereby converts chitin into chitosan. A convenient method of obtaining chitosan from the chitin found in shellfish waste is described in U.S. Pat. No. 3,862,122 (Peniston). Although there is a continuum of compositions possible between pure poly-N-acetyl-D-glucosamine and pure poly-D-glucosamine, the term chitosan is generally applied to those polymers containing 65–100% of D-glucosamine residues. As noted above, compositions within this range are soluble in acidic solutions; but if more than about 35% of the monomer residues are N-acetyl-D-glucosamine, the polymer is insoluble in weakly acidic solutions.

Commercially available chitosan is typically prepared from shellfish and has a molecular weight measured in the hundreds of thousands, corresponding to polymer chains in which several thousand monomer units are linked together in β-1,4 fashion. Chitosan obtained from fungal sources is typically of somewhat lower molecular weight and may contain fractions with molecular weight as low as 50,000 amu (atomic mass units, daltons). As used herein, the term chitosan refers to copolymers of D-glucosamine and N-acetyl-D-glucosamine containing 0–35% N-acetyl-D-glucosamine residues having a molecular weight greater than 50,000 amu. Thus, chitosan preparations in which deliberate efforts have been made to lower the molecular weight below 50,000 amu by causing chain scission with an acid or an enzyme catalyst are excluded. The chitosan used in this study was obtained from shrimp or crab shell, and contained about 75–82 mole % D-glucosamine residues, which is typical of commercially produced chitosan. It was readily soluble in dilute aqueous solutions of mineral and carboxylic acids. Because of the slower rate of dissolution caused by the high viscosities of high molecular weight chitosan in such solutions, and, indeed, the low fluidity of these viscous solutions, it is preferred that the molecular weight of the chitosan not exceed about 600,000 and preferably still not more than 350,000.

Suitable acids for making the chitosan salts for use in the invention are those acids which form water-soluble salts with chitosan. It is not necessary that the acid itself be water-soluble; however, such water-soluble acids are preferred because of ease in handling them. Inorganic acids, which form water-soluble chitosan salts, include the halogen acids and nitric acid, but exclude sulfuric and phosphoric acids because they do not form water-soluble salts with chitosan. Organic acids are preferred and include lactic acid, glycolic acid, glutamic acid, formic acid, acetic acid and mixtures thereof. Either mono-or poly-functional carboxylic acids can be used. They can be aliphatic or aromatic, so long as they form water-soluble salts with chitosan.

It will be recognized that the exposure of acidic chitosan solutions for extended periods of time at elevated temperatures is likely to result in considerable degradation of the chitosan polymer by chain scission. While chitosan polymer degradation does not in itself render the invention inoperable, its effectiveness may be reduced by extreme degradation with a significantly lower average molecular weight. Therefore, it is preferred that the reaction temperature and time be adjusted so that the extent of chitosan degradation does not result in the chitosan's becoming soluble in water below pH 7. That is, the chitosan should remain water-insoluble for maximum effect. The threshhold of the solubility of chitosan in water at pH 7 is about 50,000.

B. Additives

As used herein, the term "additives" refers to materials which may optionally be used to augment the effectiveness of the invention, but do not themselves have bio-activity. These include such materials as surfactants, coalescing agents, wetting agents, defoaming agents, extenders, penetrants, activators, spreading agents, diluents, odorants, brightening agents and the like. It is particularly preferred to use a small amount of wetting agent in the compositions in order to obtain even distribution and wetting of the hydrophobic surface of the plant leaves. Such agents are usually used in concentrations of 0.01–0.1% by weight in the applied chitosan salt soluton.

C. Coadjuvants

As used herein, the term "coadjuvant" refers to optionally added materials that have a bio-activity that may be the same or different than the bio-activity of the chitosan salts. Such materials include fertilizers, fungicides, insect repellants, pesticides, trace nutrients, herbicides, and mixtures thereof. Both liquid and solid coadjuvants can be used in conjunction with water-soluble chitosan salts, so long as the resultant aqueous compositions are sprayable.

D. Method for Making Chitosan Salt

A preferred method for making the chitosan salt is to form an aqueous dispersion of chitosan at a temperature of 30°–85° C. and preferably at 35°–70° C. and then to add the acid to the dispersion. Under these reaction conditions, the particle size of the chitosan is not critical. It is preferred that the reaction temperature be at least 45° C. in order to have a rapid rate of depression of the viscosity and salt formation without the necessity of using a large excess of acid. On the other hand, it is also preferred that the reaction temperature not exceed 85° C. in order to avoid discoloration and to assure stability of the water-soluble salt. Additives and coadjuvants can be added to the reaction solution at any stage. Nevertheless, it is preferred that they be added after the reaction is complete and the solution has cooled in order to minimize any secondary reactions.

The chitosan salt solutions prepared in the above manner are mildly acidic (pH about 4–5) and contain only about 0.5–6 wt. % of the dissolved chitosan salt. However, these solutions are more concentrated than necessary or desirable for most applications of the invention. Therefore, the thusly prepared solutions are diluted with water to reduce the concentration of the salt to the range of 0.01–1.5 wt. % desired for most applications. Nevertheless, to reduce shipping costs from the site of manufacture to the site of use, it is preferred to ship to the user the undiluted solution and instruct the user to dilute the solution to the specified application concentration at or near the site of use. The diluted aqueous solution of chitosan salt usually has a pH of about 4.5–5.5.

E. Method of Application

One clear advantage of the invention is that the chitosan salt can be applied to the plants by liquid spraying, which is the most economical and efficient method of application for both large and small agricultural areas. The aqueous compositions can be applied by other liquid application methods such as brushing, however, they are less efficient.

As mentioned above, compositions of the invention are applied to the first true leaves of the growing plant and at least twice again before harvesting of the plant, preferably at flowering and at the onset of maturation. While beneficial results on yield may be observed by even a single application of the invention to plants having their first true leaves, it has been found that a plurality of subsequent applications before harvest is most productive. Optimum results have been obtained by the application of up to four or more treatments between the emergence of the first true leaves and harvest at intervals of 2–3 weeks between such treatments. The volume of treating solution should always be sufficient to wet the exposed surfaces of the foliage on each plant. Therefore, the volume of treating solution used in such supplemental applications should be increased to provide for coverage of the increased amount of foliage which is grown prior to harvest. The last application is preferably made no later than 3–5 days before harvest.

The method of the invention is, of course, more efficient if the treated leaf surfaces are coated with a substantially continuous coating of the treating solution. However, the invention remains effective, albeit with reduced efficiency, with less than complete coverage of the leaf surfaces. It is nevertheless preferred that at least 50% of the available leaf area be coated with treating solution.

It will be recognized that the above-described chitosan salts can be used in combination with the non-phytotoxic acid salts disclosed by Freepons.

F. Safety

A further advantage of the invention is that the chitosan compositions, as applied, are non-toxic. For example, chitosan glutamate has an acute oral $LD_{50}$ of more than 5 g/kg in rats (5 male, 5 female albino rats). Furthermore, the compositions have an acute dermal $LD_{50}$ greater than 2 g/kg on rabbits (5 male, 5 female albino rabbits). Because of such low toxicity, the compositions of the invention are not toxic to birds, mammals, or humans. Moreover, the low toxicity level and easy biodegradability of the compositions act to prevent detrimental effects on the beneficial constituents of fertile soil layers. Accordingly, the Environmental Protection Agency in the U.S.A. has established an exemption from the requirement of a tolerance for residues of poly-D-glucosamine when they are used in the production of raw agricultural commodities.

G. Test Procedures

An aqueous chitosan acetate solution was prepared by vigorously stirring an appropriate amount of water at a temperature of 60 C. and adding small flakes of chitosan containing 80 mole % D-glucosamine residues at such a rate that the chitosan became wetted and dispersed throughout the liquid phase. Glacial acetic acid was then added to the chitosan solution so that the weight ratio of acetic acid to chitosan was 0.36. This represents a ratio of 1.03 equivalents of acetic acid per mole of amino function in the chitosan. The mixture was stirred at 60 C. until substantially all the chitosan had dissolved, and the resulting solution was then filtered through coarse cheese cloth to remove any adventitious particles. The quantities of water and chitosan were chosen so that the chitosan concentration (exclusive of the acetate anion) was 5.0% wt. This solution was then further diluted with water to a concentration of 2.5% wt., and packaged in several units each containing 304 g. for transport to the field. On-site dilution of the package provided the correct amount of chitosan to fill a 2 gallon (9.1 liters) garden sprayer with a solution containing 0.1% wt. chitosan.

For crops that were planted as seed (squash, cucumber, bean), treatment was commenced as soon as the seedling had produced its first set of true leaves. The true leaves are those which follow the emergent leaves (cotyledons) and resemble the leaves of the mature plant in shape. For crops that were obtained as established greenhouse seedlings (peppers), treatment was commenced at the time of transplanting outdoors. In either case, the treatment was repeated at intervals of two to three weeks throughout the growing season. The treatment protocol was to spray the foliage of the plant until the top of the leaf surfaces were thoroughly wetted and solution began to drip from the leaf tips. To the extent possible, this treatment was performed just after irrigation so that there was no substantial difference in moisture available to the treated plants compared to the controls. As the plants increased in size, it was obviously necessary to use more chitosan salt solution to wet the leaves. It was estimated that the treatment rate was 5–10 gallons/acre $(5.6-11.2) \times 10^{-3}$ liters/m$^2$) for the initial treatment and 15–50 gallons/acre $(16.9-56.2) \times 10^{-3}$ liters/m$^2$) at the end of treatment, depending on the plant and foliage. For crops that are optimally harvested before the mature stage, such as cucumbers and squash, the number of fruits, rather than total weight, was used as the measure of enhanced production. For crops that are harvested at maturity, such as beans, celery and lettuce, total crop weight was used as the measure of enhanced production.

H. Treatable Plants

A wide variety of cotyledonous plants can be advantageously treated by the method of the invention, so long as the treatment is carried out in the manner described above. Such plants include members of the genera Allium, Appium, Asparagus, Beta, Brassica, Capsicum, Citrullis, Cucurbita, Daucus, Frageria, Lactuca, Lycopersicum, Phaseolus, Solanum, Spinachia and Zea Among the members of these genera of vegetables are asparagus, beans, beets, broccoli, carrots, celery, corn, egg plant, lettuce, melons, onions, pea, peppers, potatoes, spinach, squash, strawberries and tomatoes.

EXAMPLES

Example 1

Hills of squash (Burpee Yellow Summer) each containing three plants were planted side-by-side in late May, 1996, in soil that had been prepared simply by turning and breaking up clods. All hills were cultivated and irrigated in identical fashion as required during growth. One hill was treated with chitosan salt solution by the procedure described above, and the other served as control. Fruits were harvested as they reached preferred size between July 9 and July 21. The study was terminated on July 21 due to an infestation of borers. The treated plants afforded 19 fruits compared to only 15 fruits for the control. This represents a yield enhancement of 27%.

Example 2

Parallel rows of green beans were planted in identical fashion in late May, 1996, in soil that had been prepared by turning, breaking up clods, and raking smooth. Both rows were cultivated and irrigated as required during growth. One row was treated with chitosan salt solution, as described above, while the other served as control. The crop was harvested at weekly intervals until August 26, when it was judged that the plants were spent. The treated row produced 15 lb 8 oz (6.8 kg) of beans compared to 11 lb 6 oz (5.2 kg) for the control. This represents a yield enhancement of 36%.

Example 3

Pepper plants (Lady Bell) were obtained commercially as seedlings approximately 5 inches tall and were transplanted in late May, 1996, to soil that had been turned and raked smooth. All plants were cultivated and irrigated in identical fashion throughout the growing season. Three plants were treated with chitosan salt solution as described above, while another three served as controls. Fruits were harvested as they reached preferred size throughout the growing season. The treated plants afforded a total of 46 fruits compared to 31 for the control. This represents a yield enhancement of 48%.

Example 4

Parallel rows of yellow beans were planted in identical fashion in late May, 1996, in soil that was prepared by turning, breaking up clods, and raking smooth. Both rows were cultivated and irrigated as required during growth. One row was treated with chitosan salt solution as described above, while the other served as control. The crop was harvested at weekly intervals until July 24 when it was judged that the plants were spent. The treated row produced 10 lb (4.5 kg) of beans compared to 9 lb (4.5 kg) for the control. This represents a yield enhancement of 11%.

What is claimed is:

1. A method for preparing an aqueous liquid solution having an acidic pH suitable for the treatment of plants having leaves capable of photosynthesis to improve the health and yield of the treated plants comprising:

(1) forming an aqueous liquid solution having an acidic pH comprising 0.5–6.0 wt. % of a water-soluble salt of chitosan prepared by reaction at an elevated temperature of a water-soluble chitosan, having a molecular weight no higher than about 600,000, with a water-soluble, monobasic organic acid, which may be substituted with other than halogen or amine groups, for a time and at a temperature sufficient to effect substantially complete reaction of the chitosan without degrading the chitosan to such an extent that it becomes water-soluble, in which solution the ratio of acid equivalents to amino groups derived from the chitosan is 1.01–1.20; and (2) raising the pH of the chitosan salt solution from step (1) to a level of 4.2–6.2 by diluting the solution with water having a pH of about 7.

2. The method of claim 1 in which the reaction of the chitosan and acid is carried out at a temperature of 30°–85° C.

3. The method of claim 1 in which the chitosan has a molecular weight of 50,000–300,000.

4. The method of claim 1 in which the monobasic organic acid is selected from lactic, glycolic, glutamic, tartaric, acetic, aspartic acids and mixtures thereof.

5. The method of claim 4 in which the monobasic organic acid is admixed with up to 50 wt. % of a non-monobasic organic acid, which is non-phytotoxic with respect to the leaves of the treated plant.

6. The method of claim 1 in which the chitosan salt solution is diluted with water to a pH of 4.5–5.5.

7. A method for improving the health and yield of growing cotyledonous plants having leaves capable of photosynthesis comprising:

(1) applying to the exposed surfaces of the leaves a coating of the diluted salt solution of claim 1; and (2) repeating step (1) at least two times before harvesting the plant.

8. The method of claim 7 in which the application of the treating solution to the exposed surface of the leaves of the treated plant is carried out 2–7 times at intervals of 2–3 weeks before harvest of the treated plant.

9. The method of claim 7 in which the last application of treating solution is made 2–3 days before harvest.

10. The method of claim 7 in which the treatment is carried out on plants which are subjected to multiple harvests.

11. The method of claim 7 in which the acid is selected from the group consisting of lactic, glycolic, glutamic, tartaric, acetic and aspartic acids, and mixtures thereof.

12. The method of claim 7 in which the monobasic organic acid is admixed with up to 50 wt. % of a non-monobasic organic acid which is non-phytotoxic with respect to the leaves of treated plant.

13. The method of claim 7 in which the chitosan salt solution is diluted with water to a pH of 4.5–5.5.

* * * * *